(12) United States Patent
Cahen et al.

(10) Patent No.: US 11,771,633 B2
(45) Date of Patent: Oct. 3, 2023

(54) HAIR COLORING OR BLEACHING COMPOSITION WITH REDUCED ODOR

(71) Applicant: Noxell Corporation, Hunt Valley, MD (US)

(72) Inventors: Christine Marie Cahen, Bonn (DE); Manfred Schmitt, Bensheim (DE); Moussa Barhoum, Frankfurt (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/327,221

(22) PCT Filed: Sep. 6, 2017

(86) PCT No.: PCT/US2017/050318
§ 371 (c)(1),
(2) Date: Feb. 21, 2019

(87) PCT Pub. No.: WO2018/048933
PCT Pub. Date: Mar. 15, 2018

(65) Prior Publication Data
US 2019/0175476 A1 Jun. 13, 2019

(30) Foreign Application Priority Data

Sep. 6, 2016 (EP) .................................. 16187308

(51) Int. Cl.
*A61K 8/49* (2006.01)
*A61K 8/19* (2006.01)
(Continued)

(52) U.S. Cl.
CPC ............. *A61K 8/498* (2013.01); *A61K 8/19* (2013.01); *A61K 8/22* (2013.01); *A61K 8/37* (2013.01);
(Continued)

(58) Field of Classification Search
None
See application file for complete search history.

(56) References Cited

U.S. PATENT DOCUMENTS 5,273,550 A * 12/1993 Prota ................ A61K 8/44
8/405
2006/0207037 A1 9/2006 Fadel et al.
2009/0226389 A1 * 9/2009 Warr ................. A61K 8/35
424/62

FOREIGN PATENT DOCUMENTS

EP 1133982 A2 9/2001
EP 1707185 A1 10/2006
(Continued)

OTHER PUBLICATIONS

"European Application Serial No. 16187308.8, Extended European Search Report dated Apr. 13, 2017", 12 pgs.
(Continued)

*Primary Examiner* — Bethany P Barham
*Assistant Examiner* — Barbara S Frazier
(74) *Attorney, Agent, or Firm* — Dennemeyer & Associates LLC; Victoria Friedman

(57) ABSTRACT

The present invention relates to a hair colouring and/or bleaching composition comprising at least a first aqueous component (i) and a second aqueous component (ii) being mixed prior to application onto hair, wherein the first aqueous component (i) comprises, in a cosmetically acceptable carrier one or more oxidizing agent(s), and the second aqueous component (ii) comprises, in a cosmetically acceptable carrier, one or more alkalizing agent(s) selected from the group consisting of ammonia, its salts and mixtures thereof wherein the first component (i) or the second component (ii) or both comprise at least a first and a second malodor suppressant and optionally one or more further malodor suppressants, or the first component (i) comprises
(Continued)

at least a first malodor suppressant and the second component (ii) comprises at least a second malodor suppressant, the first and the second malodor suppressant and any further malodor suppressant forming a malodor suppressant system in the hair colouring and/or bleaching composition, and each of the first and second malodor suppressants being a compound having a distribution coefficient log P of 2 or more and a molecular weight of between 100 and 400. The invention further relates to a hair colouring or bleaching kit comprising an individually packaged first and second aqueous component, a method of treating hair, a method of sequential oxidative hair colouring or hair bleaching and the use of at least a first and a second malodor suppressant as a malodor suppressant system in a composition for the treatment of hair.

10 Claims, 2 Drawing Sheets

(51) Int. Cl.
*A61K 8/22* (2006.01)
*A61K 8/37* (2006.01)
*A61Q 5/08* (2006.01)
*A61Q 5/10* (2006.01)
*A45D 19/00* (2006.01)

(52) U.S. Cl.
CPC .................. *A61Q 5/08* (2013.01); *A61Q 5/10* (2013.01); *A45D 19/0066* (2021.01); *A45D 2200/25* (2013.01); *A61K 2800/87* (2013.01); *A61K 2800/884* (2013.01)

(56) References Cited

FOREIGN PATENT DOCUMENTS

| | | |
|---|---|---|
| JP | 2001011495 A | 1/2001 |
| JP | 2002363049 A | 12/2002 |
| WO | WO-2005110499 A1 | 11/2005 |
| WO | WO-2016058710 A1 | 4/2016 |
| WO | WO-2018048933 A1 | 3/2018 |

OTHER PUBLICATIONS

"International Application Serial No. PCT/US2017/050318, International Search Report dated Nov. 10, 2017", 4 pgs.
"International Application Serial No. PCT/US2017/050318, Written Opinion dated Nov. 10, 2017", 9 pgs.

* cited by examiner

HAIR COLORING OR BLEACHING COMPOSITION WITH REDUCED ODOR

PRIORITY

This application is a U.S. National Stage Filing under 35 U.S.C. 371 from International Application No. PCT/US2017/050318, filed on Sep. 6, 2017, and published as WO 2018/048933 on Mar. 15, 2018, which application claims the benefit of priority from EP Patent Application No. 16187308.8, filed on Sep. 6, 2016, which are herein incorporated in their entirety by reference.

FIELD OF THE INVENTION

The present invention relates to a hair colouring and/or bleaching compositions.

BACKGROUND OF THE INVENTION

The permanent alteration of the colour of keratinous fibers, in particular human hair, by the application of hair dyes is well known. In order to provide the consumer with the hair colour and the intensity of the colour desired, very complex chemical processes are utilized. Permanent hair colouring formulations typically comprise oxidative hair dye precursors, which can diffuse into the hair through the cuticle and into the cortex where they can then react with each other and suitable oxidizing agents to form the end dye molecule. Due to the larger size of these resultant molecules they are unable to readily diffuse out of the hair during subsequent washing with water and/or detergent; hence delivering a consumer-desired permanency of colour. This reaction typically takes place at pH from about 8.5 to about 10.5 (approximately pH 10) in the presence of an alkalizing agent and an oxidizing agent.

Despite the fact that commercial hair colouring products have been available for many years, the products still exhibit a number of consumer-related deficiencies.

Typically, permanent hair dye products will contain an alkaline compound or at least a compound generating an alkaline compound under specific circumstances, typically a source of ammonia. This serves the purpose of swelling the hair allowing the entry of the dye precursor molecules into the hair and also improves the lightening effect of the oxidizing agent, which is typically hydrogen peroxide. Ammonia shows the best hair colouring and/or bleaching performance as well as hair damage profile, versus alternative alkalizing agents. However, ammonia is also volatile and its associated odour is extremely unpleasant to the consumers of such products, particularly as these hair colouring and/or bleaching products are used in close proximity to the nasal region. Hence, it would be highly desirable to provide an oxidative hair colouring and/or bleaching composition, and kit thereof, which delivers the consumer required lightening level and color but which has reduced or eliminated the detectable ammonia odour.

A number of attempts have been described in the literature to address the above identified improvement areas. For example, it has been described hair colouring and/or bleaching compositions comprising carbonate and/or carbamate compounds. There have also been described hair colouring and/or bleaching compositions comprising an alkalizing agent, alternative to ammonia and its salts, such as mono-ethanolamine. It has also been described to use compounds blocking and/or antagonizing the odour of ammonia. However these previous attempts have not proven fully satisfactory vis-à-vis further criteria, as they may exhibit a limited hair colouring and/or bleaching performance including limited colour delivery, uptake and/or durability; significant damages to the hair including brittle fiber formation.

SUMMARY OF THE INVENTION

There is the need thereof for providing a composition comprising ammonia and/or salts thereof, which releases a reduced odour or no odour, especially upon application onto hair. There is also the need for providing a composition comprising ammonia and/or its salts thereof, which releases a reduced or no odour, while containing sufficiently high amounts of ammonia in order to provide superior hair treatment performance. There is also the need for providing a composition comprising ammonia and/or salts thereof, releasing a reduced odour or no odour, without imparting significant damages onto the hair fibers.

Particularly, there is the need thereof for providing a composition releasing a reduced or no ammonia odour, upon application onto hair. There is also the need for providing a composition releasing a reduced or no ammonia odour, while providing superior hair colouring and bleaching performance. There is also the need for providing a composition releasing a reduced or no ammonia odour, without imparting significant damages onto the hair fibers.

The inventors have now found that a combination of two malodor suppressants with specific features regarding their distribution coefficient and their molecular weight provides for a significantly reduced or even eliminated malodor in hair coloring or bleaching compositions.

The present invention relates to a hair colouring and/or bleaching compositions comprising at least a first aqueous component (i) and a second aqueous component (ii) being mixed prior to application onto hair, wherein the first aqueous component (i) comprises, in a cosmetically acceptable carrier one or more oxidizing agent(s), and the second aqueous component (ii) comprises, in a cosmetically acceptable carrier, one or more alkalizing agent(s) selected from the group consisting of ammonia, its salts and mixtures thereof wherein the first component (i) or the second component (ii) or both comprise at least a first and a second malodor suppressant and optionally one or more further malodor suppressants, or the first component (i) comprises at least a first malodor suppressant and the second component (ii) comprises at least a second malodor suppressant, the first and the second malodor suppressant and any further malodor suppressant forming a malodor suppressant system, in the hair colouring and/or bleaching composition, and each of the first and second malodor suppressants being a compound having a distribution coefficient log P of 2 or more and a molecular weight of between 100 and 400.

The invention further relates to a hair colouring or bleaching kit comprising an individually packaged first aqueous component (i) comprising, in a cosmetically acceptable carrier one or more oxidizing agent(s) and an individually packaged second aqueous component (ii) comprising in a cosmetically acceptable carrier one or more alkalizing agent(s) selected from the group consisting of ammonia, its salts and mixtures thereof.

Another object of the invention is a method of treating hair comprising the steps of applying a composition after mixing according to the invention, or a composition obtainable as a mixture from a kit according to the invention to the hair, leaving said composition on the hair for from 2 to 60 minutes and subsequently rinsing said composition from the hair, a method according to claim 16 wherein said composition is retained on the hair for a time period of less than 50 minutes and a method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition according to the invention, or obtainable as a mixture from a kit according to the invention, applying said composition to the harr and retaining said composition on the hair for a time period of less than 50 minutes and subsequently rinsing said composition from, the hair.

In one aspect, the present invention relates to a hair colouring and/or bleaching composition comprising at least a first aqueous component (i) and a second aqueous component (ii) being mixed prior to application onto hair, wherein:

the first aqueous component (i) comprises, in a cosmetically acceptable carrier:
one or more oxidizing agent(s) and the second aqueous component (ii) comprises, in a cosmetically acceptable carrier:
one or more alkalizing agent(s) selected from the group consisting of ammonia, its salts and mixtures thereof, wherein the first component (i) or the second component (ii) or both comprise at least a first and a second malodor suppressant and optionally one or more further malodor suppressants, or the first component (i) comprises at least a first malodor suppressant and the second component (ii) comprises at least a second malodor suppressant, the first and the second malodor suppressant and any further malodor suppressant forming a malodor suppressant system in the hair colouring and/or bleaching composition, and each of the first and second malodor suppressants being a compound having a distribution coefficient log P of 2 or more and a molecular weight of between 100 and 400.

In another aspect, the present invention relates to a hair colouring or bleaching kit comprising an individually packaged first aqueous component (i) comprising, in a cosmetically acceptable carrier one or more oxidizing agent(s) and an individually packaged second aqueous component (ii) comprising in a cosmetically acceptable carrier one or more alkalizing agent(s) selected from the group consisting of ammonia, its salts and mixtures thereof, wherein the first component (i) or the second component (ii) or both comprise at least a first and a second malodor suppressant and optionally one or more further malodor suppressants, or the first component (i) comprises at least a first malodor suppressant and the second component (ii) comprises at least a second malodor suppressant, the first and the second malodor suppressant and any further malodor suppressant forming a malodor suppressant system in the hair colouring and/or bleaching composition, and each of the first and second malodor suppressants being a compound having a distribution coefficient log P of 2 or more and a molecular weight of between 100 and 400.

In still another aspect, the present invention relates to a method of treating hair comprising the steps of applying a composition after mixing of two components according to the invention or a composition obtainable as a mixture from a kit according to the invention to the hair, leaving said composition on the hair for from 2 to 60 minutes, e.g., from 5 to 50 minutes and subsequently rinsing said composition from the hair.

In still another aspect, the present invention relates to a method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition according to the invention or obtainable as a mixture from a kit according to the invention, applying said composition to the hair and retaining said composition on the hair for a time period of less than 50 minutes and subsequently rinsing said composition from the hair. In another aspect, the present invention relates to the use of said composition and/or kit for colouring and/or bleaching hair with a reduced or no ammonia odour.

DETAILED DESCRIPTION OF THE INVENTION

Figure 1:
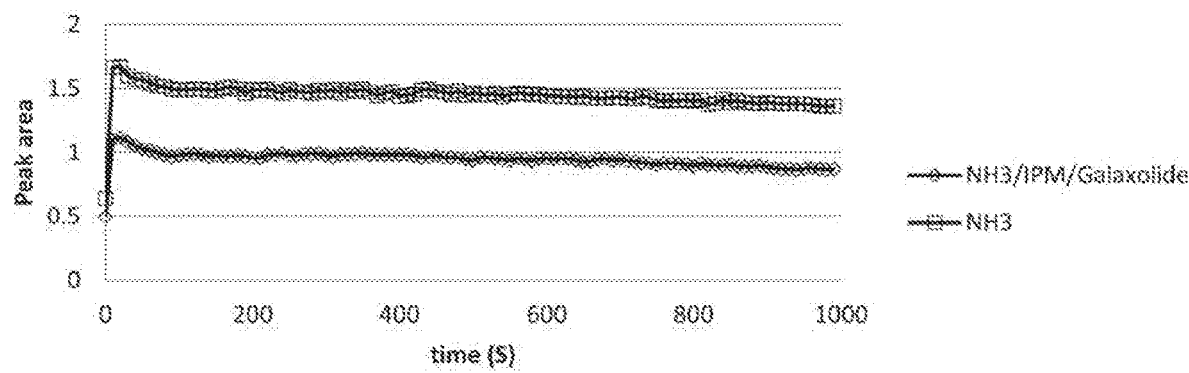
FIG. 1 shows the ammonia release kinetic of the 2.41% NH3 solution and the 2.15% NH3 solution with Galaxolide/IPM without stirring in the vessel (Examples 1 and 2). The sample with IPM/Galaxolide shows a lower ammonia release. Since a film of the nonpolar liquid was observable on the solution, it might be a physical effect.

As used herein the term "hair" to be treated may be "living" i.e. on a living body or may be "non-living" i.e. in a wig, hairpiece or other aggregation of non-living keratinous fibers. Mammalian, such as human hair is preferred. However wool, fur and other keratin containing fibers are suitable substrates for the compositions according to the present invention.

By "hair colouring" composition, it is meant a composition suitable for changing the colour of hair. The hair colouring composition is referred hereinafter as "the composition," unless otherwise specified. The hair colouring composition may comprise oxidative dye precursors, direct dyes or even no, or substantially no, dyes in case of bleaching only compositions where the change of colour is mainly caused by the degradation of the natural melanin contained in the hair shaft by the oxidizing agent. The term "hair colouring" composition as used herein covers hair bleaching and hair oxidative dyeing or direct dyeing products.

All percentages are by weight of the hair colouring composition, i.e. of the ready-to-use composition which is the composition to be applied on hair, unless otherwise specified. When a ready-to-use composition is prepared by mixing two or more components comprising ingredients to be mixed for the desired effect, the amount of these ingredients is generally provided based on the weight of the component comprising such an ingredient, in case of the present text, e.g., component (i) and component (ii).

When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

In a first aspect, the present invention relates to a hair colouring and/or bleaching composition comprising at least a first aqueous component (i) and a second aqueous component (ii) being mixed prior to application onto hair.

The first aqueous component (i) and the second aqueous component (ii) may be mixed prior to application to hair in a ratio ranging from 5:1 to 1:5, e.g., from 3:1 to 1:3 or from 2:1 to 1:2, in some cases it may be preferred to mix them in a ratio of about of 1:1

The first aqueous component (i) comprises, in a cosmetically acceptable carrier one or more oxidizing agent(s). Any oxidizing agent known in the art may be used. Oxidizing agents include for example water-soluble peroxygen oxidizing agents. As used herein, "water-soluble" means that in standard conditions at least 0.1 g, such as 1 g, such as 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

The first aqueous component may comprise a total amount of oxidizing agents ranging from 0.1% to 12%, alternatively from 1% to 9%, alternatively from 2% to 6%, by total weight of the composition.

Suitable water-soluble oxidizing agents include, but are not limited to: inorganic peroxygen materials capable of yielding hydrogen peroxide in an aqueous solution. Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, perearbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

In a specific embodiment, the composition comprises a water-soluble oxidizing agent selected from the group consisting of hydrogen peroxide, perearbonates (which may be used to provide a source of both oxidizing agent and carbonate ions and or ammonium ions), persulphates, and mixtures thereof; alternatively a water-soluble oxidizing agent being hydrogen peroxide.

The second aqueous component (ii) comprises, in a cosmetically acceptable carrier one or more alkalizing agent(s) selected from the group consisting of ammonia, its salts and mixtures thereof. The group can, e.g., consist of ammonia, ammonium halides, ammonium sulfate, ammonium phosphate, ammonium lactate, ammonium glycinate, ammonium aspartate, ammonium nitrate, ammonium perchlorate, ammonium carbonate, ammonium hydrogen carbonate, ammonium silicate, ammonium borate, and mixtures of two or more thereof. The group can further consist of ammonia, ammonium carbonate, and mixtures thereof; It can be preferred, if the the alkalizing agent is ammonia or the alkalizing agent is ammonium carbonate. If both present, the ammonium ions and the carbonate ions are present in the second aqueous component (ii) at a weight ratio of from 3:1 to 1:10, alternatively from 2:1 to 1:5.

The second aqueous component (ii) may comprise a total amount of alkalizing agents ranging from 0.1% to 12%, alternatively from 1% to 9%, alternatively from 2% to 6%, by total weight of the composition.

According to the invention, the first component (i) or the second component (ii) or both components (i) and (ii) can essentially be solutions, dispersions, emulsions or gels, they can be unstructured or even structured, e.g., comprise a gel system consisting of multi-lamellar sheets or multi lamellar vesicles or both with a wide variety of interlayer dimensions, e.g., showing a d-spacing (interlayer spacing between sheets) between 5 nm and 60 nm, or 8 nm to 50 nm, or 10 nm to 30 nm as measured by Small Angle X-Ray Scattering (SAXS).

Such presence of multi-lamellar sheets or multi lamellar vesicles can easily be confirmed via electron microscopy. Multi-lamellar sheets can usually be observed as elongated sheet like structures, which can be essentially straight or slightly curved or bent. Multi lamellar vesicles are observable as small, generally rounded or elliptical structures with a comparatively small spatial extension.

A component according to the invention can comprise one or more fatty alcohols. The fatty alcohols may be selected from the group consisting of linear and/or branched C12 to C30 fatty alcohols; e.g., from the group consisting of cetyl alcohol, stearyl alcohol, cetearyl achohol, behenyl alcohol, any mixtures of two, three or more thereof. The component may comprise from 0.5% to 20%, alternatively from 2% to 10%, alternatively from 4% to 8%, of fatty alcohol by total weight of the composition. The amount of each particular fatty alcohol or mixtures thereof described herein before can account for up to 100% (or 100%) of the total amount of fatty alcohol(s) in the composition.

The composition can comprise a non-ionic surfactant. The non-ionic surfactant may be selected from the group consisting of polyoxyethylene C12 to C30 alkyl ethers. It can be preferred if the non-ionic surfactant is selected from the group consisting of polyoxyethylene C12 to C30 alkyl ethers having at least 25 ethylene oxide units, e.g., from the group consisting of polyoxyethylene C12 to C30 alkyl ethers having from 2 to 300 ethylene oxide units, or from the group consisting of polyoxyethylene C12 to C30 alkyl ethers having from 20 to 200 ethylene oxide units, e.g., from the group consisting of ceteareth-25, steareth-20, steareth-100, steareth-150, steareth-200, and mixtures of two or more thereof. Other non-ionic surfactants which can optionally be used according to the invention are polyethyleneglycol fatty acid esters, polyoxyethylene castor oil, polyoxyethylene hydrogenated castor oil, polyoxyethylene fatty amides and their monoethanolainine and diethanolamine derivatives and polyethoxylated fatty amines, and mixtures thereof.

Alternatively, the non-ionic surfactant(s) may be free of polyethyleneoxide chains. Representative examples of non-ionic surfactants free of polyethyleneoxide chains include polyglycerolated fatty acids, polyglycerolated fatty amides, polyglycerolated alkyl phenols, polyglycerolated [alpha]-diols, polyglycerolated alcohols, alkyl polyglucosides, sugar esters and mixtures thereof.

The component may comprise from 0.1% to 20%, e.g., from 0.2% to 10%, or from 0.4% to 5%, of non-ionic surfactant by total weight of the overall composition. As all nonionic surfactants may be present in one of components (i) or (ii) it may thus be that component (i) comprises from 0.1% to 5%, e.g., from 0.2% to 3%, or from 0.4% to 1.5%, of non-ionic surfactant or component (ii) comprises from 0.1% to 5%, e.g., from 0.2% to 3%, or from 0.4% to 1.5%, of non-ionic surfactant.

Any of the components (i) or (ii) or both may, in some cases, comprise a phosphate ester compound selected from the group consisting of alkyl phosphate esters, alkoxylated alkyl phosphate esters, and mixtures thereof. The phosphate ester compound may be selected from the group consisting of C12 to C30 alkyl phosphate esters, alkoxylated C12 to C30 alkyl phosphate esters, and mixtures thereof, e.g., from the group consisting of C12 to C18 alkyl phosphate esters, alkoxylated C12 to C18 alkyl phosphate esters, and mixtures thereof, or from the group consisting of oleth-3 phosphate, oleth-5 phosphate, oleth-10 phosphate, cetoleth-5 phosphate, cetoleth-10 phosphate, trideceth-5 phosphate, trideceth-6 phosphate, trideceth-10 phosphate, cetyl phosphate, dicetyl phosphate, oleyl phosphate, dioleyl phosphate, stearyl phosphate, C9-15 alkyl phosphate, ceteareth-2 phosphate, ceteareth-20 phosphate, ceteth-10 phosphate, deceth-4 phosphate, glycereth-26 phosphate, PPG-5-ceteth-10 phosphate, steareth-2 phosphate, DEA-oleth-3 phosphate, DEA-oleth-3 phosphate, PEG-5 ethylhexyl ether phosphate, and mixtures thereof, or from the group consisting of PPG-5-ceteth-10 phosphate, oleth-3 phosphate, oleth-10 phosphate, ceteth-10 phosphate, dicetyl phosphate, cetyl phosphate, stearyl phosphate, ceteareth-2 phosphate, and mixtures thereof or from the group consisting of ceteth-10 phosphate, dicetyl phosphate, ceteareth-2 phosphate, and mixtures thereof. It is also possible that a component comprises mixtures of two or more compounds from two or more alternative groups.

Commercially suitable raw materials include materials of the Crodafos™ Series from Croda, particularly Crodafos™ CES, Crodafos™ CS2A. Crodafos™ CES comprises cetearyl alcohol, dicetyl phosphate, ceteth-10 phosphate. Crodafos™ CS2A comprises ceteareth-2-phosphate. The composition may comprise from 0.01% to 40%, alternatively from 0.1% to 20%, alternatively from 1% to 10%, alternatively from 2% to 8% of the phosphate ester compound by total weight of the composition.

It can be preferred that the composition is free of any phosphate ester compound other than the phosphate ester compound selected from the group consisting of alkyl phosphate esters, alkoxylated alkyl phosphate esters, and mixtures thereof.

The first component (i) or the second component (ii) or both comprise at least a first and a second malodor suppressant and optionally one or more further malodor suppressants, or the first component (i) comprises at least a first malodor suppressant and the second component (ii) comprises at least a second malodor suppressant, the first and the second malodor suppressant and any further malodor suppressant forming a malodor suppressant system in the hair colouring and/or bleaching composition, and each of the first and second malodor suppressants being a compound having a distribution coefficient log P of 2 or more and a molecular weight of between 100 and 400

It is essential for the present invention that the composition available after mixing components (i) and (ii) comprises at least two different malodor suppressants. It is thus possible that component (i) already comprises both necessary malodor suppressants or that component (ii) already comprises both necessary malodor suppressants, while the respective remaining component comprises no malodor suppressant at all. It is, however, also possible that each of components (i) and (ii) comprises one malodor suppressant which, after mixing components (i) and (ii) to form the hair colouring or bleaching composition, forms a mixture of at least two malodor suppressants according to the invention. It is further possible that one of components (i) and (ii) comprises one malodor suppressant and the other remaining component (ii) comprises two or more malodor suppressants or vice versa. It is further possible that that each of components (i) and (ii) comprises two or more malodor suppressants which, after mixing components (i) and (ii) to form the hair colouring or bleaching composition, forms a mixture of at least two malodor suppressants according to the invention. Generally, the mixture of two or more malodor suppressants is called a "malodor suppressant system".

In the fields of organic and medicinal chemistry, a distribution (P) coefficient is the ratio of concentrations of a compound in the two phases of a mixture of two immiscible solvents at equilibrium. Hence these coefficients are a measure of differential solubility of the compound between these two solvents. One of the solvents chosen is water while the second is octanol. Hence the partition coefficient is a measure of how hydrophilic ("water loving") or hydrophobic ("water fearing") a chemical substance is. The partition coefficient is the ratio of concentrations of un-ionized compound between the two solutions. The logarithm of the ratio of the concentrations of the un-ionized solute in the solvents is called log P:

$$\log P_{oct/wat} = \log\left(\frac{[\text{solute}]_{octanol}}{[\text{solute}]_{water}^{un-ionized}}\right).$$

It can be preferred if in a hair colouring and/or bleaching composition according to the invention the first and the second malodor suppressant comprise at least one functional group selected from the group consisting of keto group, aldehyde group, ether group, ester group or hydroxyl group or two or more of such groups, either of the same type or of one or more different types.

While generally all types and combinations of malodor suppressants according to the teaching of the present invention provide for a reduced malodor of the claimed hair colouring and/or bleaching composition, it has proven to be advantageous in many cases if at least the first malodor suppressant has a log P (octanol/water) of less than 9. In a further embodiment of the invention at least the first and the second malodor suppressant have a log P (octanol/water) of less than 9.

It is also possible that a hair colouring and/or bleaching composition according to the invention comprises a first malodor suppressant being a compound having a distribution coefficient log P (octanol/water) of 2 or more and a molecular weight of between 100 and 400 and at least a second malodor suppressant being a compound having a distribution coefficient log P (octanol/water) of 3 or more and a molecular weight of between 100 and 400, the first malodor suppressant and the second malodor suppressant being different compounds and at least one of the first and second malodor suppressants being liquid at 23° C. and 1013 mbar and the first and second malodor suppressant forming a solution upon mixing.

It has further been found that a hair colouring and/or bleaching composition according to the invention has especially good malodor suppression features, if the density of the malodor suppressant system present in the mixture of component (i) and (ii) divided by the density of the mixture of component (i) and (ii) without the malodor suppressant system is 1.1 or less. The term "malodour suppressant system" relates, as already explained above, explicitly to the sum of all single malodor suppressants being present in the claimed hair colouring and/or bleaching composition. Thus, the "malodour suppressant system" according to the invention at least contains two different malodour suppressants, but can also contain more than two malodour suppressants, e.g., three, four, five or six different malodour suppressants, forming the "malodour suppressant system".

The density mentioned above is thus measured for the "malodour suppressant system", and is advantageously about 1.1 or less, and should advantageously be higher than about 0.85. Advantageous density ranges of the should be from about 1.09 to about 0.87 or about 1.05 to about 0.88 or about 1.01 to about 0.9 or about 1.0 to about 0.92. All density values in this text relate to a temperature of 23° C. and a pressure of 1.013 bar.

Density measurements are typically performed by determining the weight and the volume of the compound to be measured or according to any other processes known to the skilled person.

Generally, it has proven to be successful if the first and second malodor suppressants are selected from the group consisting of (hereinafter called: list of malodor suppressants) isopropylmyristate, galaxolide, habanolide, Operanide, Okoumal, Silkolide, Musk Plus, Helvetolide, Romandolide, Celestolide, Scentenal, HYDROXYCITRONELLAL, o-Cresol, Para Cresol, linalool oxide (furanoid), Coumarone, METHYL BENZOATE, Canthoxal, Cyclopidene, Methyl Octalactone, ISO BUTAVAN, Ethyl valerate, natural (US), Hexyl Aldehyde, BENZYL METHYL ETHER, Isopimpinellin, HYDROXYOL, TRIFERNAL, p-Tolyl acetate, ALLYL PHENOXY ACETATE, METHYL ANTHRANILATE, Eugewhite, 4-PHENYL-2-BUTANOL, Dihydroisophorone, Gardamide, 3-Hexenyl acetate, CIS 3 HEXENYL ACETATE, CYCLOHEXYL ETHYL ALCOHOL, PHENOXL ETHYL PROPIONATE, 5-METHYL-3-HEPTANONE, 3-Heptanol, 4-Vinylphenol, METHYL AMYL KETONE, ISO PROPYL 2-METHYLBUTYRATE, METHYL HEPTENONE, 4-Ethylguaiacol, Ultravanil, Furfuryl methyl sulfide, Methyl Laitone, METHOXY MELONAL, DIMETHYL BENZYL CARBINOL, 2-ISOPROPYL-N,2,3-TRIMETHYLBUTYRAMIDE, BENZYL METHOXYETHYL ACETAL, Methoxyisobutylpyrazine, 2-ISOPROPYL-4-METHYL THIAZOLE, Benzoin, KOUMALACTONE, Pyranol, Indoflor Crist., FLOREX, trans-Cinnamic acid, Cinnamyl formate, KEONE, 8-HYDROXY PARA-CYMENE, LINALOOL OXIDE, Spirodecane, PHENYL ETHYL ACETATE, PHENYL ETHYL ACETATE, 2-ISOBUTYLTHIAZOLE, 2,4-dimethyl phenol, ETHYL TIGLATE, Ethyl Phenyl Acetate, BUCCOXIME, Verbenone, Verbenone, METHYL PHENYL CARBLNYL ACETATE, CINNAMALVA, Cinnamyl nitrile, OXANE, 4-Isopropylbenzyl alcohol, BENZYL PROPIONATE, 2-Heptanol, Methyl Cinnamate, ETHYL METHYL PHENYL GLYCIDATE, p-TOLYL ACETATE, HELIOTROPIN DIETHYL ACETAL, p-Butyrylphenol, Amyl Vinyl Carbinol, Agarbois, MUGUESIA, METHYL SALICYLATE SYNTHETIC, D-Dihydrocarvone, mixture of isomers, d-p-8(9)-Menthen-2-one, trans-Dihydrocarvone, INDOL, BENZYL ETHYL ETHER, NONALACTONE, Nonalactone, cis-Limonene oxide, METHYL JASMONATE, ETHYL 2 METHYL PENTANOATE, Pentanoic acid, 2-methyl-ethyl ester (S)-2, cis-Tagetone, EUGENOL, Hexyl formate, Nerolione, MONTAVERDI, CAMPHOR GUM, (5E)-2,6-Dimethyl-1,5,7-octatrien-3-ol, THUJONE, ETHYL AMYL KETONE, Longozal, Ionone Epoxide Beta, METHYL HEXYL KETONE, Methyl Lavender Ketone, 2,10-Epoxypinane, Amyl Acetate, AMYL-ACETATE (isomer blends), Butyl butyrate, Cis-6-Nonen-1-OL FCC, (E,Z)-3,6-nonadien-1-ol, 3,6-NONADIEN-1-OL, 3'6-NONadien-1-ol, PHENOXY ETHYL ISO BUTYRATE, 2,6-Nonadien-1-ol, CIS-3-HEPTENYL ACETATE, cis-3-HEXENYL PROPIONATE, Heptanal, Ocimenol, ISO EUGENOL ACETATE, (E)-Isoeugenol, cis-iso-Eugenol, ISO EUGENOL, MYRTENAL, DIMETHYL ANTHRANILATE, 3-Propylidenephthalide, 4-METHYL QUINOLINE, Para Methyl Quinoline, ALLYL AMYL GLYCOLATE, CINNAMYL ACETATE, cis-Sabinol, DL-BORNEOL, iso borneol, PERILLA ALDEHYDE, skatole, 4-Ethylphenol, P-ETHYL PHENOL, Eugenyl Acetate, Hydratropic Aldehyde Dimethyl Acetal, 2,6-Nonadien-1-al, E Z-2,6-Nonadien-1-al, e,e,-2,6-NONADIEN-1-AL, Myristicin, Leaf acetal, Leguminal, Azurone, alpha-Fenchyl Alcohol, FRUCTALATE, DIHYDRO EUGENOL, trans,trans-2,4-Nonadienal, L-Fenchone, fenchone, 3,5,5-Trimethyl-1-hexanol, DIHYDROTAGETONE, 3-Methyl-4-phenylpyrazole, Aladinate, Cyclohexvl acetate, PLICATONE, 1-Oxaspiro[5.5]undecan-4-ol, 4-methyl-, Myroxide, 1-phenyl-2-pentanol, 4-THUJANOL, Heptyl alcohol, Heptyl alcohol, Livescone, DECAHYDRO-2-NAPHTHOL, Asarone, PHENYL ETHYL DIMETHYL CARBINOL, METHYL ISO EUGENOL, PARA CRESYL METHYL ETHER, Isoamyl isobutyrate, MYRCENOL SUPER, GAMMA DECALACTONE, SAFROLE, DIETHYLPHTHALATE, DELTA DECALACTONE, Methyl Eugenol, Para Cresyl iso-Butyrate, CIS JASMONE, 2-PHENYL-3-(2-FURYL)PROP-2-ENAL, Phenethyl propionate, Melozone, Octanol-3, INDOCOLORE, Methoxycitronellal PG, Rhodinol 70, Jasmacyclene, VIOLIFF, 4-PENTENOPHENONE, d-CARVONE (SYNTHETIC) FCC, L CARVONE, L-CARVONE, BENZYL BUTYRATE, RINGONOL 50 TEC, PROPENYL GUAETHOL, 3-Cyclohexene-1-methanol, 3,5-dimethyl-, Clarycet, DELPHONE, ISO CYCLO CITRAL, beta-Terpineol, HEXYL ACETATE, Benzyl Iso Butyrate, STYRALLYL PROPIONATE, Amyl Propionate, AMYL PROPIONATE, ETHYL CAPROATE FCC, Ethyl Hexyl Ketone, DEHYDROXY LINALOOL OXIDE, TRIPLAL EXTRA, triplal extra, ETHYL CINNAMATE, cumin acetaldehyde, Plinol, Lyral, EUCALYPTOL, Anapear, 1-ethyl-3-methoxytricycloheptane, Cyclohexylmagnol, Dipropyl sulphide, METHYL DIHYDRO JASMONATE, trans-Hedione, 3,5,5-Trimethylhexanal, ISO PENTYRATE, CYCLO GALBANATE, BUTYL BUTYRYL LACTATE FCC, cis-Carveol, 1-Carveol, (+)-Dihydrocarveol, DIHYDROCARVEOL, Iso Pulegol, DIHYDRO ISO JASMONATE, LRG, Herboxane, 3,5,5-TRIMETHYLCYCLOHEXANOL, ISOAMYL BUTYRATE, Efetaal, Cantryl, ZENOLIDE, Isononanol, DIMETOL, VERDURAL B EXTRA, BENZOPHENONE, PHENYL HEXANOL, CAPRYLIC ACID (NATURAL), Isobutyl angelate, ROSAPHEN, Dimethyl Octenone, LIGUSTRAL OR TRIPLAL, para-menth-3-en-1-ol, DIHYDROTERPINEOL, PATCHON, trans-2-tert-Butylcyclohexanol, VERDOL, 2(10)-PINEN-3-OL, Fruitnat, OCTYL ALCOHOL, Magnolan, ETHYL SALICYLATE, MEFRANAL, SCLAREOLATE®, Syvertal, piperitenone, HERBAC, Milk Lactone, Menthone glyceerool ketal, ALPHA TERPINEOL, Alpha Terpineol Supra, MAJANTOL, MAJANTOL, TERPINEOL, METHYL BETA-NAPHTHYL KETONE, Octanenitrile, trans-Ocimenone, Peacholide, Rosyrane Super, delta-UNDECALACTONE FCC, Romascone, 4-Carvomenthenol, Terpinenol-4, Cinnamyl propionate, 2-SEC-BUTYL CYCLO HEXANONE, MENTHONE GLYCERIN ACETAL, CARVACROL, Thymol Crystals, ANETHOLE USP, TRANS ANETHOLE, BROMSTYROL, METHYL HEPTINE CARBONATE, LRG, PHENYL ETHYL METHYL ETHYL CARBINOL, Allyl phenethyl ether, DIHYDRO MYRCENOL, RHUBOFIX, Hydrocitronitrile, CYCLOPENTOL HC, LRG, PERILLA ALCOHOL, 2,6-Octadienal,_3,7-dimethyl-,_(E)-, CITRAL, Phenethyl butyrate, (R)-(+)-Pulegone, Isocyclogeraniol, CUMINIC ALDEHYDE, ISO BUTYL PHENYLACETATE, 1,4-Cineole, FG, MELONAL, Estragol Ex Badiane, Petiole, ROSSITOL, (+)-D-Menthol, d-Neomenthol, LAEVO MENTHOL, MENTHOL NATURAL, Menthol Racemic, neo-Menthol, 2,2,5-Trimethyl-4-hexenal, Isopropyl Quinoline, MAYOL, ETHYL OENANTHATE, Hexyl propionate, Amyl butyrate, mixture of isomers, CIS 3 HEXENYL BUTYRATE, 2 Nonen-1-al, Nonenal, ISO MENTHONE, Isomenthone, MENTHONE RACEMIC, FLOROPAL, 1-Hepten-1-ol, 1-acetate, (R)-gamma-Undecalactone, (S)-gamma-Undecalactone, UNDECALACTONE, Jasmatone, Dihydro Cyclacet, 5-PHENYL-3-METHYL-2-PENTENONITRILE, Citronitril, ISODIHYDRO LAVANDULAL FCC, 7-Ethoxy-3,7-dimethyloctanal, gamma-Terpineol, ROSALVA, Tetrahydrojasmone, Damascol 4-, 6-HYDROXYDIHYDROTHEASPIRANE, 2-Nonanol, PHENYL ETHYL ISO BUTYRATE, OCTYL ALDEHYDE, Muguol, Violet Nitrile, Orivone, P-TERT-AMYLCYCLOHEXANOL, Verdalia A, Vivaldie, LACTOJASMON, Benzyl isovalerate, CORANOL, laevo-linalool, LINALOOL, S)-(+)-Linalool, 2-nonanone, RHUBOFLOR, TETRA HYDRO LINALOOL, TETRA HYDRO MUGUOL, TETRAHYDRO-4 METHYL-2 PHENYL-2-PYRAN, Phenylethyl methacrylate, Reseda Body, 4-Chloro-3,5-Xylenol, VERDYL PROPIONATE, (±)-Lavandulol, (R)-(+)-Lavandulol, Gelsone, DIMETHYL BENZYL CARBINYL ACETATE, Isoamyl angelate, CYCLEMAX, CITROWANIL B, PELARGENE, ALLYL CAPROATE, Para Tertiary Butyl Phenol, SPIRO[FURAN-2(3H),5'-(4,7-METHANO-5H-INDENE], DECAHYDRO, Dihydroanethole, Corps Racine VS, Opalal®, OXADIENE, Cumin Nitrile, METHYL PAMPLEMOUSSE, Nonadyl, Acetal R, Benzyl Cinnamate, CITRONELLYL NITRILE, JASMOPYRANE, 3-hexen-1-yl isovalerate, CIS-3-HEXENYL ALPHA METHYL BUTYRATE, GERANIOL, GERANIOL, Methyl camomille, NEROL, DIMETHYL OCTANOL, DIMETHYL OCTANOL, CYCLOMETHYLENE CITRONELLOL, Cinnamyl isobutyrate, gamma-ionone, Undecanolide, DAMASCONE GAMMA, Nopylaldehyde, (d)-Citronellal, (l)-Citronellal, CITRONELLAL, Mugetanol, Hexenyl tiglate, 1,2-Dihydrolinaloool, dihydro-Linalool, ISO NONYL ACETATE, Cosmene, GERANYL FORMATE, NERYL FORMATE, FURFURYL HEXANOATE, Cyprisate Ci, METHYL OCTINE CARBONATE, Isoamyl phenyl ether, 2-hexylidene cyclopentanone, 10-UNDECEN-1-OL, RHUBAFURAN, CYCLABUTE, BETA NAPHTHOL METHYL ETHER, Heptyl acetate, Bornyl Acetate, ISO BORNYL ACETATE, ETHYLENE BRASSYLATE, PRENYL BENZOATE, LINALYL FORMATE, Vetiverol, VETIVEROL, HEXYL-2-FUROATE, Pomarose, Liminal, TABANON COEUR, DELTA DAMASCONE, Jasmonitrile, BARANOL, CITRONELLOL, R-(+)-B-CITRONELLOL, ISO JASMONE T, PARMAVERT, METHYL ISO BUTENYL TETRAHYDRO PYRAN, Rose Oxide L, Decenal-9, Octacetal, Iso Bergamate, IRALIA TOTAL, BENZYL BENZOATE, gamma-Dodecalactone, CYCLOBUTANATE, FRUITATE, Iso Butyl Caproate, cis-4-DECEN-1-AL-FCC, DECENAL (TRANS-4), Benzyl ether, hexyl butyrate, CITRONELLYL OXYACETALDEHYDE, delta-DODECALACTONE FCC, BUTYL BENZOATE, CYMAL, FLORHYDRAL, CITRAL DIMETHYL ACETAL, Hexyl Isobutyrate, NONYL ALDEHYDE, ETHYL SAFRANATE, Methyl geramate, Cis-3-Hexenyl Valerate, ETHYL LINALOOL, Flor_acetate, Methyl Cyclogeranate, Isobutyl benzoate, CYCLOHEXYL ETHYL ACETATE, Claritone, p-t-Butyl phenyl acetaldehyde, Para Anisyl Phenyl Acetate, Bergamal, Citronellyl Formate, Phenyl Benzoate, Dihydrojasmone, Ethyl gamma-safranate, Pivarose, Geranyl Nitrile, Cis-3-Hexenyl Tiglate, ISO BUTYL SALICYLATE, ETHYL DAMASCENATE, ethyl isopropyl bicycloheptene-2-carboxylate, ISO BUTYL QUINOLINE, Isobutyl Quinoline-2, NEOBERGAMATE FORTE, 4-tert-Butylbenzaldehyde, gamma-Terpinyl acetate, Dispirone, N-ETHYL-2-ISOPROPYL-5-METHYLCYCLOHEXANE CARBOXAMIDE, 1-Methyl-3-methoxy-4-isopropylbenzene, ALLYL HEPTOATE, Citral propylene glycol acetal, QUINCESTER, MUSK AMBRETTE, FENCHYL ACETATE, Para Cresyl Phenyl Acetate, beta-Terpinyl acetate, DIHYDROCITRONELLAL, Octanal,3,7-dimethyl-, Hexyl trans-2-butenoate, METHYL-2-NONENOATE, DIHYDRO BETA IONONE, Cressanther, n-BUTYL SALICYLATE, NEROLIN BROMELIA, PINO ACETALDEHYDE, ALPHA-BISABOLOL, 10-undecenenitrile, octanal propylene glycol acetal, Terpinyl Methyl Ether, APHERMATE, Irisnitrile, PHENYL ETHYL TIGLATE, Ethyl Caprylate, GLYCOLIERRAL, 1,8-Thiocineol, Lavandulyl acetate, TRIFONE DIPG, beta-Ionone, IONONE BETA, ALPHA DAMASCONE, alpha-damascone, gamma_methyl_ionone, Hexyl neopentanoate, Octyl acetate, Furfuryl heptanoate, BOURGEONAL, AZURIL, IONONE ALPHA, Fleursandol, Khusinil, MACEAL, Pharaone, Oxybenzone, O-Methyl linalool, Floralozone, FLORALOZONE, Andrane, GERANYL ACETATE, NERYL ACETATE, 3-Thujopsanone, TERPINYL ACETATE, 4,5,6,7-Tetrahydro-3,6-dimethylbenzofuran, Methyl Diphenyl Ether, MELAFLEUR, alpha-Phellandrene, Phenethyl 2-methylbutyrate, DAMASCENONE TOTAL, Damascenone,trans-, LEMONILE, LINALYL ACETATE, BETA PINENE, Phenyl Ethyl Benzoate, Trichloromethyl Phenyl Carbinyl Acetate, CAMPHENE, Ethyl 3,7-dimethyl-2,6-octadienoate, ISO BORNYL PROPIONATE, 2-Decene-1-al, Calyxol (Quest), TRANS-2-DECENAL, PIVACYCLENE, DIHYDRO ALPHA IONONE, Menthyl formate, SABINENE, Ambrinol 20T, EBANOL, DUPICAL, FLEURAMONE, Gyrane, Prenyl Salicylate, UNDECAVERTOL, UNDECYLENIC ALDEHYDE, Benzyl phenylacetate, AMBRINOL, Tetrahydroionol, DAMASCONE BETA, Silvial®, VELOUTONE, 4,7-Methano-1H-inden-6-ol, 3a,4,5,6,7,7ahexahydro-8,8-dimethyl-, propanoate, alpha-Fenchene, FLORAL SUPER, GALBASCONE, NONYL ALCOHOL, NEO HIVERNAL, Myrac Aldehyde, Hindmol, HINDINOL, (−)-Carvyl acetate, mixture of cis and trans, Isoamyl salicylate, mixture of isoamyl and 2-methylbutyl salicylates, L-Dihydrocarvyl acetate, mixture of isomers, FRUTONILE, 2-T-BUTYLCYCLOHEXYLOXY-2-BUTANOL, DIPHENYL OXIDE, PERILLA ACETATE, dimethyl cyclohexyl 3-butenyl ketone, POIRENATE, Isodamascone N, ALLO-OCIMENE, ALDEHYDE SUPRA, 2-p-Menthadiene, CAPRIC ACID NAT, DIMETHYL BENZYL CARBINYL BUTYRATE, CASHMERAN, CITRONELLYL ACETATE, Koavone, BENZYL ISO EUGENOL, NOOTKATONE, Butyl sulfide, Hexyl-2-Methyl Butyrate, MUSK RI, DIPHENYL METHANE, PHENYL ETHYL PHENYL ACETATE, BENZYL SALICYLATE, NOPYL ACETATE, Alicate, CINNAMYL CINNAMATE NAT, CIS-3-HEXENYL CIS-3-HEXENOATE, Gamma Terpinene, 12 OXAHEXADECECANO- LIDE, CYCLOHEXYL SALICYLATE, MUSK KETONE, Phenyl Ethyl Isoamyl Ether, Apritone, IRONE ALPHA REFINED, PARA CYMENE, FLEURANIL, ETHYL 2,4-DECADIENOATE, (+)-alpha-pinene, ALPHA PINENE, L-ALPHA PINENE, Methyl diphenyl ether, Brahmanol, Spirambrene, CIS-3-HEXENYL BENZOATE, alpha-Methyl Ionone, b-METHYL IONONE, Herbavert, cis-Pinane, METHYL NONYL KETONE, AMYL BENZOATE, Rholiate, Mefloral, P.T.BUCINAL, Wolfwood, Geranyl Propionate, GIVESCONE, ALLYL CYCLOHEXANE PROPIONATE, PEONILE, NECTARYL, LINALYL PROPIONATE, Terpinyl propionate, AMYL SALICYLATE, beta-isomethyl ionone, BORONAL, OXALIDE T, HEXYL TIGLATE, 3-Carene, AURANTIOL, IONONE, GAMMA METHYL, Datilat, DECYL ALDEHYDE, PHENAFLEUR, alpha-Sinensal, Ethyl nonanoate, 7-Methyloctyl acetate, ABIERATE CN, Isobornyl isobutyrate, (E)-β-Ocimene, cis Ocimene, OCIMENE, Neocaspirene Extra, METHYL OCTYL ACETALDEHYDE, SPIROGALBANONE, Nirvanol, POLYSANTOL, 2-Heptyl tetrahydrofuran, VELTONAL, ETASPIRENE, 2-nonanone propylene glycol acetal, Citryl acetate, GRISALVA, Belambre, CIS-3-HEXENYL SALICYLATE, Vetikol Acetate, Pinyl Iso Butyrate Alpha, 2-Undecene-1-al, Rhodalione, Citronellyl ethyl ether, alpha-Vetivone, Spathulenol, Citrathal, MYRCENE, Citronellyl Propionate, JAVANOL, LAEVO TRISANDOL, Elintaal Forte, TERPINEOLENE, OCTALYNOL, alpha-Terpinene, THESARON, Nebulone, Theaspirane, mixture of cis and trans, I-Limonene Natural, ORANGE OIL COLD PRESSED, ORANGE TERPENES, PRECYCLEMONE B, Precyclemone B, LINALYL ISO BUTYRATE, BIGARADE OXIDE, p-Cresyl n-hexanoate, FURFURYL OCTANOATE, Rosamusk, Elemol, ISO BORNYL CYCLOHEXANOL, SINENSAL, NATURAL, MIXTURE OF ALPHA & BETA, 4-TERTIARY BUTYL CYCLOHEXYL ACETATE, Menthanyl Acetate, VERDOX, Verdox HC, Vertenex, HEALINGWOOD, GERANYL ISOBUTYRATE, NERYL ISOBUTYRATE, α-Amylcinnamyl alcohol, mixture with Amyl hydrocinnamyl alcohol, SANDALORE, ETHYL-2-TERT-BUTYLCYCLOHEXYL CARBONATE, Linalyl butyrate, Mandaril, CEDROL, (+)-D-Menthyl acetate, Isomenthyl acetate, MENTHYL ACETATE, Salviac, Myraldyl acetate, beta-Vetivone, INDOLENE, Cetonal, Ysamber K, YSAMBER K, Dibenzyl, Caryolan-1-ol, Geranyl Butyrate, Dihydro Ambrate, Amyl Cinnamate, Tetrahydro Geranyl Acetate, Guaiol, AMYL CINNAMIC ALDEHYDE, beta-santalol, Hexyl hexanoate, beta-Himachalene oxide, ROMANDOLIDE, Palisandal, 3,6-Dimethyl-3-octanyl acetate, TETRAHYDRO LINALYL ACETATE, UNDECYL ALDEHYDE, Myrrhone, β-Bisabolol, ONCIDAL, Bulnesol, I-Citronellyl Isobutyrate, Nonyl Acetate, Ethyl Undecylenate, HEXALON, Cassiffix, Cassiffix, LAURIC ACID (NATURAL), Dibutyl_o-phthalate, tau-Cadinol, A-cadinol, T-Muurolol, I-Citronellyl n-Butyrate, OXYOCTALINE FORMATE, alpha-Agarofuran, (e,e)-FARNESOL, FARNESOL, ISO E SUPER OR WOOD, Boisiris®, Viridiflorol, OCTYL-2-FUROATE, MUSK TIBETENE, NEROLIDOL, HABANOLIDE, GERANYL TIGLATE, Hexyl benzoate, FIF/UL Mandannal, EXALTENONE, CEDROXYDE®, alpha-santalol, Hydroxymethyl-isolongifolene in dipropylene glycol, 10-epi-gamma-Eudesmol, HEXYL SALICYLATE, γ-Eudesmol, PHENYL ACETALDEHYDE DIMETHYL ACETAL, GALBANOLENE SUPER, Ambrocemde, (Z)-4-dodecen-1-al, NORLIMBANOL, ACALEA TBHQ, geranyl valerate, HEXYL CINNAMIC ALDEHYDE, AGRUMEA, Agruraea, Isoamyl octanoate, (E)-5-Tangerinol, (Z)-5-Tangerinol, (Z)-3-Dodecenal, Kusunol, Undecene 2 Nitrile, 7-epi-alpha-Eudesmol, alpha-Eudesmol, CEDRYL FORMATE, METHYL CEDRYLONE, Operanide, Ozofleur, TRIMOFIX O, Lauryl alcohol, SCLAREOL, METHYL NONYL ACETALDEHYDE, Ethyl Caprate, CYCLOPENTADECANONE, 1,3-Dioxane, 2-(2,4-dimethyl-3-cyclohexen-1-yl)-5-methyl-5-(l-methylpropyl)-, I-Citronellyl Tiglate, BUTYLATED HYDROXY TOLUENE, CEDRYL METHYL ETHER, Maritima, 1-Methyl-4-(1-methylethyl)-cyclohexane, p-Menthane, LAURIC ALDEHYDE, AMBRONAT, CETALOX, CLONAL, LINALYL ANTHRANILATE, Palisandin, 2,6,10-Trimethylundecanal, Nirvanolide, 2-TRIDECENAL (HIGH TRANS) FCC, DELTA MUSCENONE, Serenolide®, 5-CYCLOHEXADECEN-1-ONE, Adoxal, Amberketal IPM, SANTALEX T, BOISAMBRENE FORTE, EXALTOLIDE TOTAL, Parsol MCX, alpha-Curcumene, Curzerene, vetiveryl acetate, HELVETOLIDE, 1,1,2,3,3-Pentamethylindan, Phantolid Crystals, β-Selinene, METHYL NONYL ACETALDEHYDE DIMETHYL ACETA, Decanal diethyl acetal, CEDAC, Celestolide, alpha-Cubebene, ALPHA-AMYLCINNAMYL ACETATE, Dodecanal dimethyl acetal, CYCLOHEXADECENONE, N-Decyl Propionate, LINALYL BENZOATE, HYDROXYAMBRAN, Citronellyl benzoate, geranyl phenyl acetate, GERANYL PHENYLACETATE, beta-Patchoulline, 2-TRIDECENENITRILE, ALPHA-FARNESENE, CARYOPHYLLENE ACETATE, FARNESYL ACETATE, GERANYL BENZOATE FCC, Acetoxymethyl-isolongifolene (isomers), alpha-bisabolene, Trisamber®, delta-Elemene, Cis-Iso-Ambrettolide, Oxacycloheptadec-8-en-2-one, trans-Ambrettolide, SILVANONE CI, AMBRETTOLIDE, LAEVO MUSCONE, beta-Guaiene, I-Citronellyl Phenylacetate, beta-Sesquiphellandrene, Butyl Undecylenate, Amyl Cinnamic Aldehyde Diethyl Acetal, Iso Amyl Undecylenate, Germacrene D, Amber xtreme-Compound 2, beta-Cedrene, gamma-Gurjunene, GERANYL CAPROATE, Civettone, OKOUMAL, ethyl laurate, (−)-β-Himachalene, BISABOLENE, Lauryl acetate, alpha-Santalene, Decane, Valencene, TRIDECYL ALCOHOL, BRANCHED, 7-epi-Sesquithujene, Sclareol oxide, Vulcanolide, Selina-3,7(11)-diene, alpha-Patchoulene, TRANS-BETA-FARNESENE, CITRONELLYL CAPROATE, β-Copaene, delta-Guaiene, 7-epi-alpha-Selinene, HEXAMETHYLINDANOPYRAN, α-Selinene, Allo-aromadendrene, ISOPROPYL LAURATE, Thujopsene, γ-Cadinene, γ-Muurolene, Germacrene B, A-CARYOPHYLLENE, Amber Xtreme, alpha-Amorphene, alpha-Muurolene_2, α-Cadinene, Hexyl octanoate, γ-Himachelene, α-Bergamotene, ALDEHYDE C-14 MYRISTIC, Indolene, α-Gurjunene, Decyl anthranilate, Myristo nitrile, P.T. BUCINAL METHYL ANTHRANILATE, CARYOPHYLLENE EXTRA, HEXAHYDROFARNESYL ACETONE, alpha-Himachalene, Geranyl linalool (all trans), Cyclotetradecane, Methyl myristate, Isoamyl laurate, 1-Hexadecanol, GERANYL CAPRYLATE, LINALYL OCTANOATE, METHYL LINOLEATE, Ethyl myristate, ISO PROPYL MYRISTATE, BENZYL LAURATE, Methyl Palmitate, ETHYL PALMITATE, ISOPROPYL PALMITATE NF, Methyl stearate, Butyl stearate, HEXAROSE, and mixtures of two, three, four or more thereof, preferably isopropylmyristate, galaxolide, habanolide, Operanide, Okoumal, Silkolide, Musk Plus, Helvetolide, Romandolide, Celestolide or a mixture of three, or four or more thereof.

It can be preferred if the first malodor suppressant is selected from the group consisting of isopropylmyristate, galaxolide, habanolide or mixtures of isopropylmyristate and galaxolide or isopropylmyristate and habanolide or galaxolide and habanolide.

It can further be preferred if the second malodor suppressant is selected from the group consisting of isopropylmyristate, galaxolide, habanolide or mixtures of isopropylmyristate and galaxolide or isopropylmyristate and habanolide or galaxolide and habanolide.

It has often proven to be successful if the first and the second malodor suppressant are, e.g., isopropylmyristate and habanolide, or isopropylmyristate and galaxolide.

In a further embodiment of the invention the first and second malodor suppressants are a liquid at 23° C. and 1013 mbar In a still further embodiment of the invention in a combination of first and second malodor suppressants at least two malodor suppressants have a log P of 3 or more and a molecular weight of 100-400.

Generally the malodor suppressant system can be present in any of the components (i) or (ii) or in both components. It has, however, proven in some cases to be advantageous if the malodor suppressant is present in at least the component which comprises the ammonia compound or two or more ammonia compounds.

In a hair colouring and/or bleaching composition according to invention, the first malodor suppressant or the combination of first and second malodor suppressants is present in the first composition (i) in an amount of 0 to 70% by weight, and the combined amount of malodor suppressants in the first and second composition is at least 0.1% by weight.

Further, the first malodor suppressant or the combination of first and second malodor suppressants is present in the second composition (ii) in an amount of 0 to 70% by weight, and the combined amount of malodor suppressant in the first and second composition is at least 0.1% by weight.

It is necessary according to the invention that the malodor suppressant system is present either in component (i) or in component (ii) or results after mixing components (i) and (ii).

The viscosity of a hair coloring and/or bleaching composition according to the invention, the composition should, after mixing, have a viscosity which enables an adaption to generally all useful ways of applying the composition to the hair. This can be, e.g., a very fluid state of matter which enables a rapid application, but can also be a more viscous state, which allows for a longer residence time on the hair also under vertical conditions. Thus, it can be preferred if the hair coloring and/or bleaching composition according to the invention after mixing of compositions (i) and (ii), has a viscosity of from 1 to 2000 cPs, e.g., from 100 to 1500 cPs or from 200 to 1000 cPs. Viscosity is measured using Brookfield viscometers with cone and plate attachment. For viscosities in the range of 0 to 12000 cPs, the Brookfield DV-11 viscometer with S42 plate is used. 2 ml sample of the composition is equilibrated at 26.7° C. for three minutes before the readings are taken at 1 rpm.

The hair coloring and/or bleaching composition can further comprise fatty compound(s) selected from the group consisting of mineral oil, hydrocarbon oil, and mixtures thereof in an amount of up to 30%, by total weight of the composition, e.g., in an amount of 0.1 to 28% or 0.5 to 25% or 1 to 15% or 3 to 10% by weight. Commercially suitable raw materials include materials of the Marcol™ Series from ExxonMobile, particularly Marcol™ 52 and Marcol™ 82.

The composition comprises a cosmetically acceptable carrier or solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxy ethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxy diglycerol, dipropyleneglycol, polyglycerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least 50%, alternatively from at least 60%, alternatively from at least 70%, by total weight of the composition. Typically, when present, the composition comprises a total amount of organic solvents ranging from 1% to 30%, by total weight of the composition.

The composition may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the composition may comprise a total amount of oxidative dye precursors ranging up to 12%, alternatively from 0.1% to 10%, alternatively from 0.3% to 8%, alternatively from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5, 6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-

(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The composition may further comprise compatible direct dyes, in an amount sufficient to provide additional colouring, particularly with regard to intensity. Typically, the composition may comprise a total amount of direct dyes ranging from 0.05% to 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1,2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No, 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

The composition may further comprise one or more chelant(s) (also known as "chelating agent", "sequestering agent", or "sequestrant") in an amount sufficient to reduce the amount of metals available to interact with formulation components, particularly oxidizing agents, more particularly peroxides. Any suitable chelant known in the art may be used.

The composition may comprise a total amount of chelant(s) ranging from at least 0.01%, alternatively from 0.01% to 5%, alternatively from 0.25% to 3%, alternatively from 0.5% to 1%, by total weight of the composition.

Suitable chelant(s) include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

The composition may comprise chelant(s) selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccimc acid (EDDS), their salts thereof, their derivatives thereof, and mixtures thereof; alternatively ethylenediaminedisuccimc acid (EDDS).

The composition may further comprise one or more radical scavenger(s). As used herein the term "radical scavenger" refers to a species that can react with a radical, preferably a carbonate radical to convert the radical species by a series of fast reactions to a less reactive species. In one embodiment, the radical scavenger(s) is different from the alkalising agent and/or is present in an amount sufficient to reduce the damage to the hair during the colouring/bleaching process.

The composition may comprise a total amount of radical scavenger(s) ranging from 0.1% to 10%, alternatively from 1% by weight to 7%, by total weight of the composition.

Suitable radical scavenger(s) includes, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

The composition may further have a pH of from 3 to 13, alternatively from 8 to 12, alternatively from 9 to 11. The composition may also comprise, in addition to the alkalizing agent(s) discussed above, pH modifier(s) and/or buffering agent(s) in an amount that is sufficiently effective to adjust the pH of the composition to fall within a range from 3 to 13, alternatively from 8 to 12, alternatively from 9 to 11.

Suitable pH modifier(s) and/or buffering agent(s) include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3-propandiol); guanidium salts; alkali metal and ammonium hydroxides and carbonates; and mixtures thereof.

Further pH modifier(s) and/or buffering agent(s) include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

The composition may further comprise thickener(s) and/or rheology modifiers) in an amount sufficient to provide the composition with a viscosity so that it can be readily applied to the hair without unduly dripping off the hair and causing mess.

The composition may comprise a total amount of thickener(s) ranging from at least 0.1%, alternatively at least 0.5%, alternatively at least 1%, by total weight of the composition.

Suitable thickener(s) include, but are not limited to: associative polymers, polysaccharides, non-associative polycaxboxylic polymers, and mixtures thereof. Commercially available salt-tolerant thickeners include, but not limited to: xanthan, guar, hydroxypropyl guar, scleroglucan, methylcellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrrollidone (Povidone), Acrylates/Ceteth-20 Ttaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth-10 phosphate, Di-cetyl phosphate and Cetearyl alcohol (available as Crodafos CES), and mixtures thereof. The composition may comprise a total amount of thickener(s) selected from anionic and cationic polymer(s) of less than 2%, alternatively less than 1% by total weight of the composition.

The composition may further comprise a source of carbonate ions, carbamate ions, hydrogen carbonate ions, and mixtures thereof in a sufficient amount to reduce damage to the hair during the coloring process.

The composition may comprise a total amount of a carbonate ion source ranging from 0.1% to 13%, alternatively from 0.1% to 10%, alternatively from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

The composition may further comprise one or more conditioning agent(s), and/or be used in combination with a composition comprising one or more conditioning agent(s). Any suitable conditioning agent(s) known in the art may be used.

The composition may comprise a total amount of conditioning agent(s) ranging from 0.05% to 20%, alternatively from 0.1% to 15%, alternatively from 0.2% to 10%, alternatively from 0.2% to 2%, alternatively from 0.5% to 2%, by total weight of the composition. The conditioning agent(s) may be included in a separate pre- and/or post-treatment composition.

Suitable conditioning agent(s) include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agent(s) include mineral oils and other oils such as glycerin and sorbitol. The composition may comprise a total amount of cationic conditioning agent(s) of less than 1%, alternatively less than 0.1% by total weight of the composition.

The composition may further comprise surfactant(s), other than the non-ionic surfactant(s). Suitable surfactant(s) generally have a lipophilic chain length of from 8 to 30 carbon atoms and can be selected from anionic surfactants, amphoteric surfactants, cationic surfactants, and mixtures thereof. Any suitable surfactant(s) known in the art may be used.

The composition comprises a total amount of anionic surfactant(s) of less than 20%, alternatively less than 10%, alternatively less than 5% by total weight of the composition. Alternatively, the composition may be free of anionic surfactant(s).

The composition comprises a total amount of cationic surfactant(s) of less than 20%, alternatively less than 10%, alternatively less than 5% by total weight of the composition. Alternatively, the composition may be free of cationic surfactant(s).

The composition may comprise a total amount of surfactant(s) other than fatty alcohol(s) and non-ionic surfactant(s) of less 20%, alternatively less than 10%, alternatively less than 5%.

The composition may comprise, in addition to the ingredients indicated above, further ingredients in order to further enhance the properties of the composition, as long as these are not excluded by the claims. Suitable further ingredients include, but not limited to: solvents; peroxymonocarbonate ion sources; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.;

The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed herein below, whose disclosure is of course non-exhaustive.

The composition may be free of amine compounds and/or phospholipid compounds; alternatively may be free of fatty monoamine compounds, polyamine compounds having at least three amino groups and fatty quaternary amine compounds and/or phospholipid compounds.

The composition may comprise a total amount of polymer(s) selected from anionic and cationic polymer(s) of less than 1%, alternatively less than 0.1% by total weight of the composition. Alternatively, the composition may be free of anionic and cationic polymer(s).

The oxidizing agent(s), the alkalizing agent, the fatty alcohol(s), the non-ionic surfactant(s), the fatty compound(s) and the cosmetically acceptable carrier, to be incorporated into the first and/or the second component, have been defined hereinbefore. Likewise, any suitable optional compounds including the oxidative dye precursor(s), the direct dye(s), the chelant(s), the radical scavenger(s), pH modifier(s) and/or buffering agent(s), thickener(s) and/or rheology modifier(s), carbonate ion source(s), conditioning agent(s), surfactant(s), and any further ingredients, to be incorporated into the first and/or the second composition, have also been defined hereinbefore.

The first and the second components may be mixed for 5 sec to 3 min, alternatively for 15 sec to 2 min, alternatively for 30 sec to 1 min.

Depending on stability and reactivity considerations, the compounds may be incorporated indifferently into the first and/or the second components, or may preferably be incorporated into one of the two components. The fatty compound(s) selected from the group consisting of a mineral oil, hydrocarbon oil, and mixtures thereof when present may be incorporated into the first component, the second component being free of said fatty compound. The fatty alcohol(s) and/or the non-ionic surfactant(s) may be incorporated into the first component and/or the second component.

The oxidative dye precursors including the primary intermediates and couplers are usually incorporated into the second component. The direct dyes are usually incorporated into the second component. The chelant may be incorporated into the first and/or the second component, however the chelant is usually incorporated into the first component for stability reason.

The invention further relates to a hair colouring or bleaching kit comprising

An individually packaged first aqueous component (i) comprising, in a cosmetically acceptable carrier one or more oxidizing agent(s) and An individually packaged second aqueous component (ii) comprising in a cosmetically acceptable carrier one or more alkalizing agent(s) selected from the group consisting of ammonia, its salts and mixtures thereof, wherein the first component (i) or the second component (ii) or both comprise at least a first and a second malodor suppressant and optionally one or more further malodor suppressants, or the first component (i) comprises at least a first malodor suppressant and the second component (ii) comprises at least a second malodor suppressant, the first and the second malodor suppressant and any further malodor suppressant forming a malodor suppressant system in the hair colouring and/or bleaching composition, and each of the first and second malodor suppressants being a compound having a distribution coefficient log P of 2 or more and a molecular weight of between 100 and 400.

In the hair colouring or bleaching kit according to the invention the malodor suppressant is selected from the group of compounds described above and named "list of malodor suppressants".

Individually packaged components mean that they may be packaged in separate containers or in compartmented containers. The consumer mixes the first component and the second component together immediately before use and applies it onto the hair. The first and the second components may be mixed from 5 sec to 3 min, alternatively from 15 sec to 2 min, alternatively for 30 sec to 1 min prior application to the hair.

After working the combined mixture for a few minutes (to insure uniform application to all of the hair), the hair colouring and/or bleaching composition is allowed to remain on the hair for an amount sufficient for the dyeing to take place, usually from 2 min to 60 min, typically from 30 min to 45 min. The consumer or salon professional then rinses the hair thoroughly with water and/or shampoo and allows it to dry. It will be observed that the hair has changed from its original colour to the desired colour.

The kit may also comprise a third component selected from the group consisting of a conditioning composition, a pre-treatment composition, and/or a colour refresher composition. The pre-treatment may be applied onto hair, before applying the hair colouring and/or bleaching composition. The conditioning composition, comprising a conditioning agent, may be mixed together with the first and the second component prior to application onto hair, or may be alternatively applied separately onto hair, for example after applying the hair colouring and/or bleaching composition. The colour refresher composition, comprising optionally a pre-formed dye, may be applied after applying the hair colouring and/or bleaching composition. The component could be also a carrier for dye precursors or concentrates.

The invention also relates to a method of treating hair comprising the steps of applying a hair colouring or bleaching composition after mixing as described above or a composition obtainable as a mixture from a kit as described above to the hair, leaving said composition on the hair for from 2 to 60 minutes and subsequently rinsing said composition from the hair.

The method of colouring and/or dyeing hair comprises applying onto hair a hair colouring and/or bleaching composition as defined herein before. The method may comprise the steps of: providing a first component as defined hereinbefore; providing a second component as defined hereinbefore; mixing the first and the second components for obtaining a hair colouring and/or bleaching composition; applying the obtained composition onto hair, leaving the applied composition on hair from 5 min to 60 min, alternatively 10 min to 30 min; optionally rinsing hair using a rinsing composition, alternatively rinsing hair with water; optionally cleansing hair using a cleansing composition; optionally treating hair with a conditioning and/or treating composition; and, optionally drying hair.

The kits described hereinabove are well-known in the art and the compositions in each container can be manufactured utilizing any one of the standard approaches, these include a) 'Oil-in-water' process, b) 'Phase Inversion' process and c) 'One-pot' process. For example, the wax components of the tint base and developer are melted to 90° C., respectively. The melted wax mixture is then mixed with 90° C. preheated water and continuously stirred for 40 minutes. The resulting mixture is then allowed to slowly cool down to room temperature, e.g., at a rate of about 1° C./min to about 3° C./min, under continuous stirring. When the mixture cools down to 40° C. ammonia, perfume, perfume components for NH3 suppression, and the other non-wax components of the ingredients list are added to the mixture under continuous stirring until the mixture cools down to room temperature (25° C.). The resulting mixture is then either packed in aluminum tubes for tint or in PE bottles for developer, thus, e.g., forming the first and second component parts of a bleaching or colouring kit.

The present invention may be provided in a variety of packaging devices and/or dispensing devices. These dispensing devices can come in the form of separate devices which may be used independently or in combination with one another. Typically, the hair colouring and/or bleaching compositions are contained within separate single or multi-compartment containers so that the compositions can be stored separately from one another before use. The compositions are then mixed together by a mixing means and then dispensed from the device and applied to the consumer's hair by an application means.

The most common packaging device which can be used involves storing the developer component in a container such as a bottle, tube, aerosol, or a sachet and separately storing the dye component in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the developer component and the tint component by any means, including by using a mixing bowl and/or a mixing tool, by adding one component into the container of the other component followed by mixing, or by perforating or displacing a seal located between the separate compartments of the components within a single container or sachet followed by mixing.

The devices described herein above can also be used in combination with a product delivery and or application tool to aid application of the product onto the hair, including using a nozzle attached to one of the containers, using a separate applicator device such as a comb or brush, using a comb attached to or instead of the dispensing nozzle whereby the product is dispensed through hollow tines and dispensing apertures located in the comb tines. The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used. Additional device technology can be used to assist in the penetration of the product into the hair. Examples of such technology include heating devices, ultraviolet light devices and ultrasound devices.

The hair colouring and/or bleaching composition, and the corresponding first and second components, may be manufactured by conventional processes known in the art for manufacturing oxidative hair colouring and/or bleaching products, and ad-mixing the ingredients of each component composition in suitable vessels, followed by packaging in appropriate individual containers.

The invention further relates to a method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition as described above or obtainable as a mixture from a kit as described above, applying said composition to the hair and retaining said composition on the hair for a time period of less than 50 minutes and subsequently rinsing said composition from the hair.

In another aspect, the invention relates to the use of a hair colouring and/or bleaching composition according to the invention for colouring and/or bleaching hair with a reduced or eliminated ammonia odour.

The invention will further be described by the following experimental data.

EXPERIMENTAL

In order to determine the influence of the malodor suppressants on different ammonia containing systems, test samples were provided and analyzed.

| Tint base: | |
| --- | --- |
| Raw Materials | % weight |
| Cetaryl Alcohol | 9.5 |
| Glyceryl Stearate SE | 8 |
| Glyceryl oleate | 2 |
| Ceteareth-25 | 2 |
| EDTA disodium salt | 0.05 |
| Etidronic Acid | 0.05 |
| Sodium Sulfite | 0.05 |
| Ascorbic acid | 0.2 |
| Sodium sulfate | 0.5 |
| Ammonia solution (25%) | 4.095 |
| NH3 suppression components | 0.7 |
| Sodium Lauryl Sulfate 70% | 4 |
| Water qs | 68.855 |

The developer consists of the following raw material composition:

| Welloxon 6% | |
| --- | --- |
| Raw Materials | |
| Cetearyl alcohol | 3.4 |
| Ceteareth-25 | 0.8 |
| Etidronic acid, 85% | 0.01 |
| Phosphoric acid, 85% | 0.1 |
| Salicylic acid | 0.1 |
| Disodium phosphate | 0.08 |
| Hydrogen peroxide (50%) | 12 |
| Water qs | 83.51 |

The wax components of the tint base and developer examples are melted to 90° C. The melted wax mixture is then mixed with 90° C. pre-heated water and continuously stirred for 40 minutes. The resulting mixture is then allowed to cool down at a rate of 2° C./min to room temperature und continuous stirring.

When mixture cools down to 40° C. ammonia, perfume, perfume components for NH3 suppression, and the other non-wax components of the ingredients list are added to the creme under continous stirring till creme cools down to room temperature (25° C.). The resulting creme is then either packed in aluminum tubes for tint or in PE bottles for developer.

The total ammonia content of the following samples was analyzed (Table 1) by means of Kjeldahl analysis.

TABLE 1

| Samples | | |
|---|---|---|
| Sample type | Sample Number | Total Ammonia content % |
| 9.2% ammonia solution (25%) | 1 | 2.41 |
| 9.2% ammonia solution (25%) with 0.7% Galaxolide/IPM | 2 | 2.15 |
| Composition without Galaxolide/IPM | 3 | 1.61 |
| Composition with IPM/ Galaxolide | 4 | 1.91 |
| Composition with 0.7% IPM | 5 | 1.65 |
| Composition with 0.7% Galaxolide | 6 | 1.95 |

Method

For Samples 1 and 2, 7.5 g of the ammonia solution are mixed with 7.5 g of water. For samples 3 to 6, 7.5 g sample and a developer (Welloxon Perfect 6%) are mixed in an open bowl with a brush until homogeneous. The time until homogeneity was reached was taken for the first sample samples were mixed for the time taken for the respective first sample. The obtained mixture is then transferred manually into a 1 l 3-neck round vessel with a KPG-stirrer which is then sealed. The headspace above the mixture is then continuously driven through a gas cell by constant introduction of ambient air into the vessel, and analyzed by means of FTIR (with background correction for ambient air). A kinetic profile is recorded using the absorption bands of ammonia at 926 cm−1 and 966 cm−1 for 1000 seconds. In addition, the total ammonia is absorbed in a boric acid solution in order to quantify the total release by acidimetric titration.

Experiments

The following samples were analyzed:
1.
   NH3 solution of sample 1 without stirring
   NH3 solution of sample 1 with stirring
2.
   0.7% Galaxolide/IPM mixture in NH3 solution of sample 2 without stirring
   0.7% Galaxolide/IPM mixture in NH3 solution of sample 2 with stirring
3.
   Composition without Galoxolide/IPM (sample 7) without stirring in the vessel, initial mixing time of tint and developer: 40 sec. Not 20 sec because of the viscosity of the NGN chassis.
   Composition with Galaxolide/IPM (sample 8) without stirring in the vessel, initial mixing time of tint and developer: 40 sec.
   Composition with 0.7% IPM without stirring in the vessel, initial mixing time of tint and developer: 40 sec.
   Composition with 0.7% Galaxolide without stirring in the vessel, initial mixing time of tint and developer: 40 sec.
4.
   Composition without Galoxolide/IPM with stirring in the vessel, initial mixing time of tint and developer: 40 sec. Not 20 sec because of the viscosity of the NGN chassis.
   Composition with Galaxolide/IPM with stirring in the vessel, initial mixing time of tint and developer: 40 sec.
   Composition with 0.7% IPM with stirring in the vessel, initial mixing time of tint and developer: 40 sec.
   Composition with 0.7% Galaxolide with stirring in the vessel, initial mixing time of tint and developer: 40 sec.

Experiment 1 and 2: 7.5 g solution is diluted with 7.5 g water, respectively.
Experiment 3 and 4: 7.5 g tint is mixed with 7.5 g Welloxon Perfect 6%, respectively.

Figure 2:
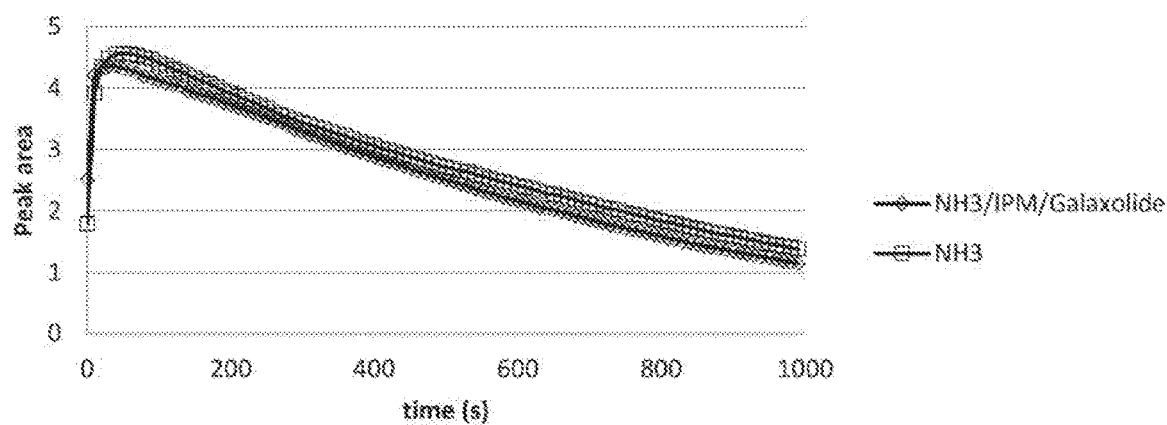
FIG. 2 shows the behavior of the ammonia release kinetic with stirring. No significant differences are observable, which supports the assumption of a physical effect in FIG. 1.
Figure 3:
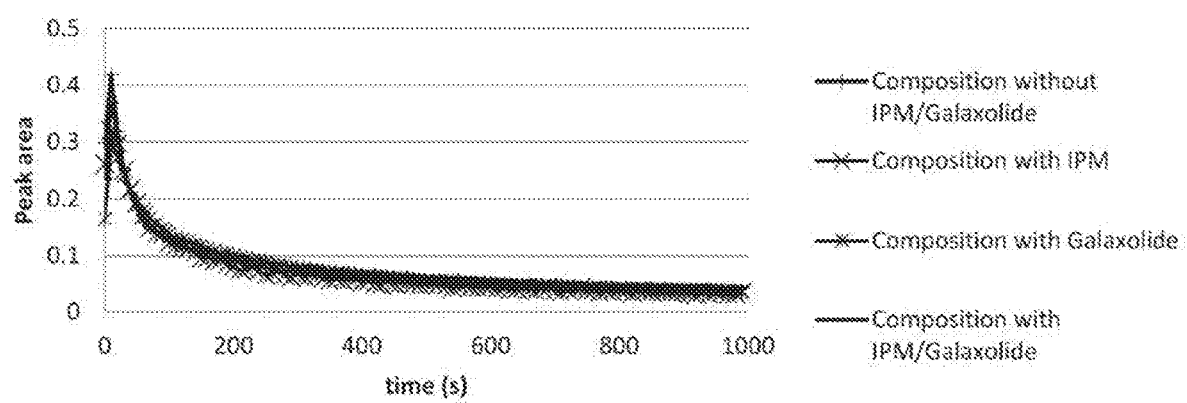
FIG. 3 shows the ammonia release kinetic of the composition with Welloxon 6% (Experiments 3 and 4) without stirring.
Figure 4:
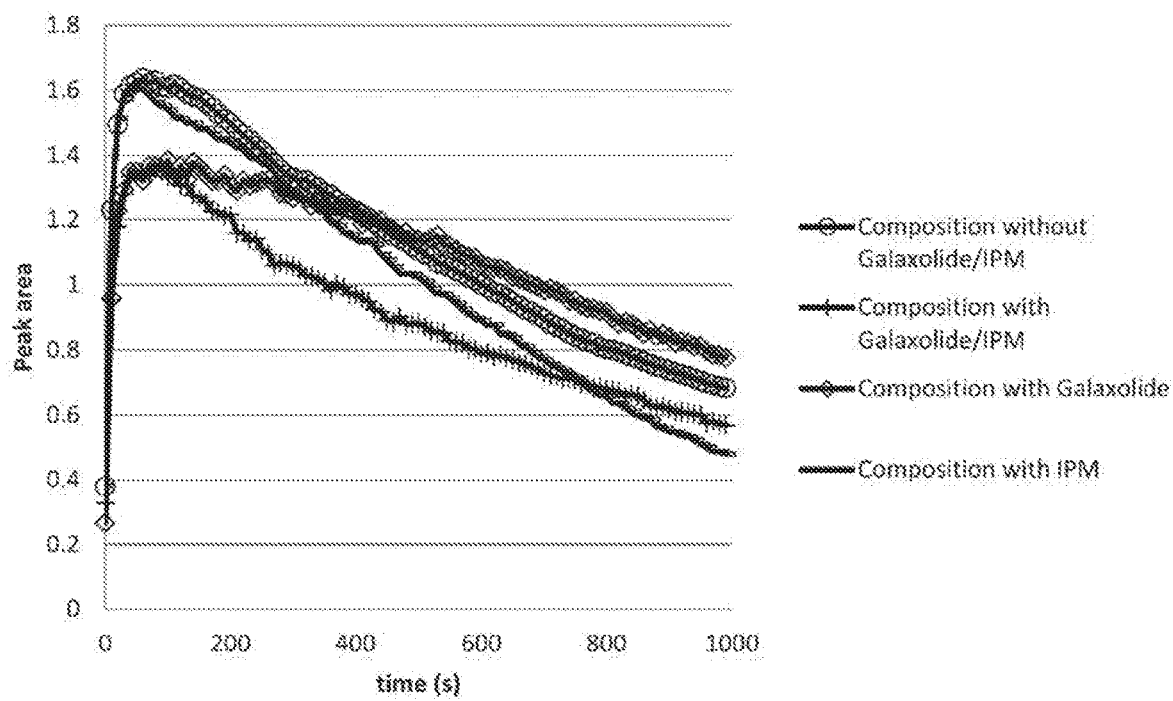
FIG. 4 shows the ammonia release kinetics of a composition with stirring.

The results of the measurements are shown in FIGS. 1 to 4. The absolute peak area values of different figures are not directly comparable and do not allow for a conclusion on an absolute effect. The peak area values of measurements within a single figure are directly comparable and do allow for a conclusion on an absolute effect.

It is clearly visible that the Ammonia release with the combination of malodor suppressants according to the invention is significantly lower in the first 1000 seconds.

Total Ammonia Release

Table 2 and Table 3 show the total ammonia content of the samples, analyzed via Kjeldahl and the total ammonia released within 1000 s measuring time. Every experiment consists of two measurements.

TABLE 2

| Total ammonia release with stirring in the vessel | | |
|---|---|---|
| | NH3 solution | NH3/Galaxolide/IPM |
| NH3 content % | 2.41 | 2.15 |
| NH3 content Released within 1000 s % | 1.82 | 1.65 |
| Ratio % | 75.5 | 76.7 |

| | Composition without Galaxolide/ IPM | Composition with Cataxolide/ IPM | Composition with IPM | Composition with Galaxolide |
|---|---|---|---|---|
| NH3 content % | 1.61 | 1.91 | 1.65 | 1.95 |
| NH3 content Released within 1000 s % | 0.64 | 0.57 | 0.71 | 0.71 |
| Ratio % | 39.8 | 29.8 | 43.0 | 36.4 |

The examples show that the combination of malodor suppressants according to the invention results in a significant drop in ammonia release.

A panel test was performed with 5 panelists with trained expertise in the classification of ammonia smells. The panelists received a mixture of tint and developer as described under GN and NGN above (stirred by a single operator for all tests until mixture was homogeneous). The panelists were asked to rate the ammonia smell according to a scale of 0 to 5, the mixture being passed from panelist to panelist with an additional stirring for each of the panelists.

TABLE 3

| Panel test | | | |
|---|---|---|---|
| Tint | Developer | Mixing Ratio | Rating |
| Composition | Welloxon | 1:1 | 3-4 |
| Composition with 0.7% Galaxolide | Welloxon | 1:1 | 3-4 |
| Composition with 0.7% IPM | Welloxon | 1:1 | 3-4 |
| Composition with 0.35% Galaxolide and 0.35% IPM | Welloxon | 1:1 | 1-2 |

0 = no Ammonia Smell
5 = Harsh Ammonia Smell

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A hair coloring and/or bleaching composition comprising at least a first aqueous component (i) and a second aqueous component (ii) being mixed prior to application onto hair, wherein:
    the first aqueous component (i) comprises, in a cosmetically acceptable carrier: one or more oxidizing agent(s), one or more fatty alcohols and a polyoxyethylene C12-C30 alkyl ether and
    the second aqueous component (ii) comprises, in a cosmetically acceptable carrier: one or more alkalizing agent(s) selected from the group consisting of ammonia, its salts and mixtures thereof, one or more fatty alcohols and a polyoxyethylene C12-C30 alkyl ether, and optionally one or more oxidative dyes or one or more direct dyes or a mixture of one or more oxidative dyes and one or more direct dyes,
    wherein the second aqueous component (ii) comprises a mixture of a first and a second malodor suppressant, the first and the second malodor suppressant forming a malodor suppressant system in the hair coloring and/or bleaching composition,
    wherein the mixture of first malodor suppressant and second malodor suppressant is equal weight percentages of isopropyl myristate and Galaxolide at a mixture concentration in the second aqueous component (ii) to provide a concentration of the mixture of isopropyl myristate and Galaxolide in the mixture of the first aqueous component (i) and the second aqueous component (ii) of to about 0.7 wt %; and,
    wherein a mixture of the first and second aqueous components exhibits a decrease of the amount of gaseous ammonia released relative to the combination of first and second aqueous components without the first and second malodor suppressants.

2. A hair coloring and/or bleaching composition according to claim 1 wherein the density of the malodor suppressant system present in the mixture of components (i) and (ii) divided by the density of the mixture of components (i) and (ii) without the malodor suppressant system is 1.1 or less.

3. A hair coloring and/or bleaching composition according to claim 1 wherein the first and second malodor suppressant form a solution upon mixing.

4. A hair coloring or bleaching composition according to claim 1, wherein said composition after mixing components (i) and (ii) has a viscosity of from 1 to 2000 cPs.

5. A hair coloring or bleaching composition according to claim 1, wherein said composition after mixing components (i) and (ii) has a viscosity of from 100 to 1500 cPs.

6. A hair coloring or bleaching composition according to claim 1, wherein said composition after mixing components (i) and (ii) has a viscosity of from 200 to 1000 cPs.

7. A hair coloring or bleaching kit comprising
    An individually packaged first aqueous component (i) comprising, in a cosmetically acceptable carrier one or more oxidizing agent(s), one or more fatty alcohols and a polyoxyethylene C12-C30 alkyl ether and
    An individually packaged second aqueous component (ii) comprising in a cosmetically acceptable carrier one or more alkalizing agent(s) selected from the group consisting of ammonia, its salts and mixtures thereof, one or more fatty alcohols and a polyoxyethylene C12-C30 alkyl ether,
    wherein the second aqueous component (ii) comprises a mixture of a first malodor suppressant and a second malodor suppressant, the first and the second malodor suppressant forming a malodor suppressant system in the hair coloring and/or bleaching composition,
    wherein the mixture of first malodor suppressant and second malodor suppressant is equal weight percentages of isopropyl myristate and Galaxolide at a mixture concentration in the second aqueous component (ii) to provide a concentration of the mixture of isopropyl myristate and Galaxolide in the mixture of the first aqueous component (i) and the second aqueous component (ii) of to about 0.7 wt %; and,
    wherein a mixture of the first and aqueous components exhibits a decrease of the amount of gaseous ammonia released relative to the combination of first and second aqueous components without the first and second malodor suppressants.

8. A method of treating hair comprising the steps of applying a composition after mixing according to claim 1 to the hair, leaving said composition on the hair for from 2 to 60 minutes and subsequently rinsing said composition from the hair.

9. A method according to claim 8 wherein said composition is retained on the hair for a time period of less than 50 minutes.

10. A method of sequential oxidative hair coloring or hair bleaching comprising the steps of at least two sequential oxidative hair color or hair bleaching treatments, wherein the time period between each treatment is from 1 day to 60 days, and wherein each treatment comprises the steps of providing a composition according to claim 1, applying said composition to the hair and retaining said composition on the hair for a time period of less than 50 minutes and subsequently rinsing said composition from the hair.

* * * * *